United States Patent [19]

Corvers et al.

[11] Patent Number: 4,577,023

[45] Date of Patent: Mar. 18, 1986

[54] DIAZABICYCLO (2,2,2) OCTADIONES

[75] Inventors: Antonius Corvers, Beek; Johannes H. A. Hofman, Elsloo, both of Netherlands

[73] Assignee: Stamicarbon B.V., Geleen, Netherlands

[21] Appl. No.: 614,241

[22] Filed: May 25, 1984

Related U.S. Application Data

[63] Continuation-in-part of Ser. No. 442,975, Nov. 19, 1982, abandoned.

[30] Foreign Application Priority Data

Nov. 21, 1981 [NL] Netherlands ..................... 8105277
Nov. 19, 1982 [CA] Canada ............................ 415988

[51] Int. Cl.⁴ .......................................... C07D 471/08
[52] U.S. Cl. .................................................. 546/122
[58] Field of Search ......................... 546/122; 544/282

[56] References Cited

U.S. PATENT DOCUMENTS 3,905,979  9/1975  Henry et al. ................ 260/268 BF
3,947,445  3/1976  Henry et al. ................ 260/268 BF
3,951,980  4/1976  Henry et al. ................ 260/268 BF

OTHER PUBLICATIONS

Jerry March, "Advanced Organic Chemistry: Reactions, Mechanism, and Structure," McGraw Hill, New York, 1968, pp. 338-339.
Journal of Chemical Society, Chemical Communications, "Intramolecular Cycloaddition of Olefine Bonds . . .", pp. 502-503, (1975).
Journal Chemical Society, Perkin Trans., II, pp. 1293-1297, (1978).
Journal of Heterocyclic Chemistry, No. 11, pp. 449-451, (1979).
Journal Medical Chemistry, No. 17, pp. 481-487, (1974).

Primary Examiner—Henry R. Jiles
Assistant Examiner—Bernard I. Dentz
Attorney, Agent, or Firm—Cushman, Darby & Cushman

[57] ABSTRACT

Disclosed are diazabicyclo (2,2,2) octadiones having the formula:

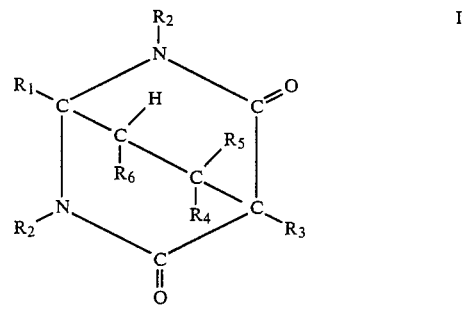

wherein $R_1$–$R_6$ are independently selected from the group consisting of hydrogen, methyl, and ethyl.

A method for synthesizing the compounds shown above is also disclosed and consists essentially of:

A. reacting a compound having the formula:

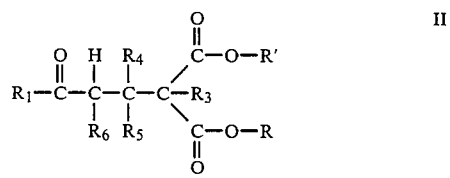

wherein R and R' are independently selected from the group consisting of hydrogen and alkyl or cyclo alkyl having 1 to 10 carbon atoms, and $R_1$–$R_6$ are independently selected from the group consisting of hydrogen, methyl, and ethyl, with B. a reactant selected from the group consisting of ammonia and primary amines having the formula $R_2$–$NH_2$ wherein $R_2$ is selected from the group consisting of hydrogen, methyl, and ethyl. The disclosed compounds can be used as starting materials for preparing the corresponding octanes which octanes exhibit useful biological activity, particularly as blood pressure depressants.

9 Claims, No Drawings

DIAZABICYCLO (2,2,2) OCTADIONES

RELATED APPLICATIONS

The present application is a continuation in part of U.S. application Ser. No. 442,975, filed on Nov. 19, 1982, which parent application is now abandoned.

FIELD OF THE INVENTION

This invention relates to a group of new diazabicyclo(2,2,2)octadione compounds and to a process for their preparation.

BACKGROUND OF THE INVENTION

The U.S. Pat. No. 3,167,561 describes 2,5-diazabicyclo(2,2,2)octadiones as starting materials for the preparation of the corresponding octanes. These diazabicyclo(2,2,2)-octanes, in both the unsubstituted and N-substituted forms, find application as antihistamines, antiemetics, antiallergics, tranquillizers, antiparasitics, hypotensive agents, central nervous system depressants, sedatives, antibiotics, spasmolytics, analgesics, central nervous system stimulants, and the like.

SUMMARY AND DESCRIPTION OF THE INVENTION

This invention provides a new group of compounds having the following general formula:

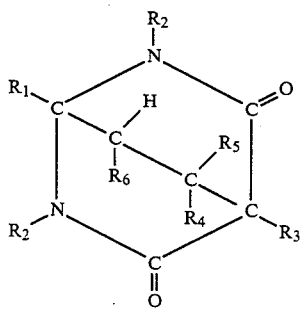

wherein $R_1$ to $R_6$ are independently selected from the group consisting of hydrogen, methyl, and ethyl. These compounds, then, are substituted or unsubstituted 2,6-diazabicyclo(2,2,2)octa-3,5-diones. According to a preferred embodiment of this invention, $R_1$ is an ethyl or methyl group. According to another preferred embodiment of this invention, $R_2$ is an ethyl or methyl group.

Specific representatives examples of compounds obtained in accordance with this invention are:
1-methyl-2,6-diazabicyclo(2,2,2)octa-3,5-dione,
1,2,6-trimethyl-2,6-diazabicyclo(2,2,2)octa-3,5-dione,
1,4-dimethyl-2,6-diazabicyclo(2,2,2)octa-3,5-dione,
1-ethyl-2,6-diazabicyclo(2,2,2)octa-3,5-dione,
1,8-dimethyl-2,6-diazabicyclo(2,2,2)octa-3,5-dione.
These compounds can be used as starting materials for preparing the corresponding octanes and said octanes exhibit useful biological activity, particularly as blood pressure depressants.

This invention further relates to a process for preparing a 2,6-diazabicyclo(2,2,2)octa-3,5-dione having general Formula I. The process is implemented by reacting, as starting material, a compound of the formula

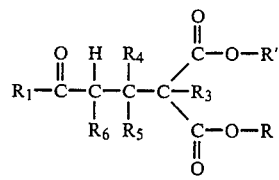

wherein R and R' are independently selected from the groups consisting of alkyl or cycloalkyl having 1 to 10 carbon atoms and hydrogen and $R_1$–$R_6$ have the meaning given above, with ammonia or a primary amine of the formula $R_2$—$NH_2$ wherein $R_2$ is also as defined above. The reaction with ammonia results in positions 2 and 6 being unsubstituted, while the reaction with a primary amine gives an N-substituted compound. For example, the starting compound may be ethyl 2-carbethoxy-5-oxocaproate. The reaction of ammonia with this compound yields 1-methyl-2,6-diazabicyclo(2,2,-2)octa-3,5-dione, along with the liberation of ethanol.

The reaction may be conducted stoichiometrically using 2 moles of ammonia or primary amine per mole of starting material, but it is advantageous to use an excess of ammonia or primary amine. It is feasible as well to conduct the reaction using a deficiency of these reactants, but this is obviously less desirable. The maximum quantity of ammonia or primary amine relative to the starting material will depend on the price of the starting amine.

In view of the nature of the reaction, R and R' should preferably be lower alkyl groups, such as methyl or ethyl.

The process may be carried out in accordance with known methods for the preparation of amides (J. March, Advanced Organic Chemistry: Reactions, Mechanisms, and Structure, McGraw-Hill Book Co., New York, 1968, pp. 338–339). The reaction may be conducted in a solvent which is inert with respect to the reaction product or, alternatively, the solvent may be the primary amine which also participates in the reaction.

It is particularly advantageous, however, to use a solvent in which the starting material is readily soluble and the reaction product is insoluble or only sparingly soluble, such that the product is precipitated during the reaction. Examples of such solvents are water and lower alkanols having 1 to 4 carbon atoms such as methanol, ethanol, and 1-propanol.

It is generally unnecessary to add a catalyst to the reaction mixture. Under certain circumstances, however, it may be advantageous to conduct the reaction at an elevated temperature and/or an elevated pressure to improve the rate and/or the yield.

After termination of the reaction the product may be isolated, for example, by distilling off the solvent or by filtering off the solids. The solids can then be washed and dried. If necessary, the diazabicyclooctadione obtained may be recrystallized one or more times e.g. from lower aliphatic alcohols with 1–3 carbon atoms. If the starting material was an ester having Formula II, the alkanol formed in the reaction may be recovered and recycled.

The starting material having Formula II may be prepared by any of a number of known methods, such as reacting an α,β-unsaturated keto compound having the formula

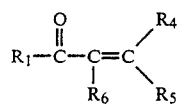

with malonic acid or a derivative thereof having the formula

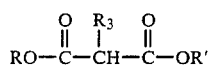

wherein R, R', and $R_1$–$R_6$ are as previously defined. For example, the reaction of butenone with diethyl malonate yields the previously mentioned ethyl-2-carbethoxy-5-oxocaproate.

The invention will now be further explained by means of the following examples. A decomposition temperature cited therein indicates that the compound decomposed before reaching a melting point.

EXAMPLE I

Preparation of 1-methyl-2,6-diazabicyclo(2,2,2)octa-3,5-dione 230 grams of ethyl-2-carbethoxy-5-oxocaproate and 270 ml of 25 weight % aqueous ammonia were mixed at room temperature in a round-bottom flask fitted with a stirrer, thermometer, and reflux condenser.

The temperature rose slowly to 34° C. as the ester dissolved. Solids started to crystallize out after about 1 hour. About 5 hours after the start of the reaction the temperature began to fall. By about 16 hours after the start of the reaction the temperature had fallen to 20° C. At this point the solids were filtered off and washed with water. After drying, 106 grams of a compound subsequently identified as 1-methyl-2,6-diazabicyclo(2,2,2)octa-3,5-dione was obtained. The yield was thus 68.8%. The compound decomposed at 250° C.

Identification of 1-methyl-2,6-diazabicyclo(2,2,2)octa-3,5-dione a. Mass spectrometry The mass spectrum for the product of Example I was recorded with AEI instruments $MS_9$ and $MS_{30}$.

The mass spectrum showed a weak peak at m/e 154. The empirical formula of a strong fragment of mass 126 was determined to be $C_5H_6N_2O_2$, as calculated from an accurate mass measurement at a resolving power of about 15000. This demonstrates that $C_2H_4$ had split off and indicates the presence of a $C_2$ bridge.

b. NMR spectrometry

The $^1H$— and $^{13}C$—NMR spectra of the compound were determined with an XL-100A Varian spectrometer at room temperature, using deuterated formic acid as solvent and TMS as reference. The results were as follows:

| | |
|---|---|
| $^1H$ NMR: | = 1.73 (s, 3, $CH_3$) |
| | = 2.10 (m, 4, $Ch_2$) |
| | = 3.60 (t, 1, CH) |
| | = 11.16 (s, 2, NH) |
| $^{13}C$ NMR: | = 19.37 ($C_9$, $^1J_{CH}$ = 28.5 Hz) |
| | = 19.9 ($C_8$, $^1J_{CH}$ = 31.5 Hz) |
| | = 33.05 ($C_7$, $^1J_{CH}$ = 30.0 Hz) |
| | = 50.0 ($C_4$ $^1J_{CH}$ = 34 Hz) |
| | = 68.4 ($C_1$, $^1J_{CH}$ = 0 Hz) |
| | = 175.1 ($C_3$, $C_5$ $^1J_{CH}$ = 0 Hz) |

Comparison of these spectra with those of the starting compounds showed that the product was 1-methyl-2,6-diazabicyclo(2,2,2)octa-3,5-dione.

In all of the following examples the structure of the reaction product was established by $^{13}C$— or $^1H$—NMR.

EXAMPLE II

Preparation of 1-methyl-b 2,6-diazabicyclo(2,2,2)octa-3,5-dione

As described in Example I, 103 grams of 1-methyl-2,6-diazabicyclo(2,2,2)octa-3-dione was obtained by reacting 202 grams of methyl 2-carbomethoxy-5-oxocaproate with 270 ml of a 25 weight % aqueous solution of ammonia after reaction for 16 hours (yield 66.9%). The compound decomposed at 250° C. Identification was established in the same manner as described in Example 1.

EXAMPLE III

Preparation of 1,2,6-trimethyl-2,6-diazabicyclo(2,2,2)octa-3,5-dione

As in Example II 24.5 grams of 1,2,6-trimethyl-2,6-diazabicyclo(2,2,2)octa-3,5-dione was obtained by reacting 38.0 grams of methyl 2-carbomethoxy-5-oxocaproate with 80 ml of a 35% aqueous solution of methylamine following distillation of the residual methylamine-water solution and recrystallization of the resulting residue from 1-propanol. The yield was 71.6%. The melting point was 162°–163° C. Identification was established as described in Example I.

EXAMPLE IV

Preparation of 1-ethyl-2,6-diazabicyclo(2,2,2)octa-3,5-dione

As in Example I, 4.1 grams of 1-ethyl-2,6-diazabicyclo(2,2,2)octa-3,5-dione was prepared by reacting 9.0 grams of ethyl 2-carbethoxy-5-oxoenanthate with 20 ml of a 25 weight % aqueous solution of ammonia. The yield was 66%. The product had a melting point (after recrystallization from ethanol) of 170°–171° C. Identification was established as described in Example I.

EXAMPLE V

Preparation of 1,4-dimethyl-2,6-diazabicyclo(2,2,2)octa-3,5-dione 4.3 grams of 1,4-dimethyl-2,6-diazabicyclo(2,2,2)octa-3,5-dione was prepared from the reaction of 26 grams of ethyl 2-methyl-2-carbethoxy-5-oxocaproate with 35 ml of a 25 weight % aqueous solution of ammonia. The selectivity was 90%. The compound decomposed at 240° C. Identification was established as described in Example I.

EXAMPLE VI

Preparation of 1,2,6,8-tetramethyl-2,6-diazabicyclo(2,2,2)octa-3,5-dione

As described in Example III, 5.6 grams of 1,2,6,8-tetramethyl-2,6-diazabicyclo(2,2,2)octa-3,5-dione was obtained from 10 grams of ethyl 2-carbethoxy-3-methyl-5-oxocaproate with a yield of 70%. The melting point was 137° C. Identification was established as described in Example I.

EXAMPLE VII

Preparation of 1,2,4,6-tetramethyl-2,6-diazabicyclo(2,2,2)octa-3,5-dione

As in Example III, 5.6 grams of 1,2,4,6-tetramethyl-2,6-diazabicyclo(2,2,2)octa-3,5-dione was obtained from the reaction of 26 grams of ethyl-2-methyl-2-carbethoxy-5-oxocaproate with 40 ml of a 35 weight % aqueous solution of methylamine. The selectivity was 69.5%. 16 grams of crude starting product was also recovered. The reaction product melted at 165° C. Identification was established as described in Example I.

EXAMPLE VIII

Preparation of 1,8-dimethyl-2,6-diazabicyclo(2,2,2)octa-3,5-dione

As in Example I, 6.35 grams of 1,8-dimethyl-2,6-diazabicyclo(2,2,2)octa-3,5-dione was obtained from the reaction of 15 grams of ethyl 2-carbethoxy-3-methyl-5-oxocaproate with 30 ml of a 25 weight % aqueous solution of ammonia. The yield was 63% and the compound decomposed at 240° C. Identification was established as described in Example I.

What is claimed is:

1. A diazabicyclo(2,2,2)octadione having the formula

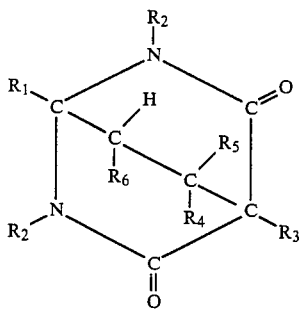

wherein $R_1$–$R_6$ are independently selected from the group consisting of hydrogen, methyl, and ethyl.

2. A diazabicyclo(2,2,2)octadione as defined by claim 1, wherein $R_1$ is selected from the group consisting of methyl and ethyl.

3. A diazabicyclo(2,2,2)octadione as defined in claim 1, wherein $R_2$ is selected from the group consisting of methyl and ethyl.

4. A diazabicyclo(2,2,2)octadione as defined by claim 1, wherein $R_1$ and $R_2$ are selected from the group consisting of methyl and ethyl.

5. A diazabicyclo(2,2,2)octadione as defined by claim 1, wherein said diazabicyclo(2,2,2)octadione is 1-methyl-2,6-diazabicyclo(2,2,2)octa-3,5-dione.

6. A diazabicyclo(2,2,2)octadione as defined by claim 1, wherein said diazabicyclo(2,2,2)octadione is 1,2,6-trimethyl-2,6-diazabicyclo(2,2,2)octa-3,5-dione.

7. A diazabicyclo(2,2,2)octadione as defined by claim 1, wherein said diazabicyclo(2,2,2)octadione is 1,4-dimethyl-2,6-diazabicyclo(2,2,2)octa-3,5-dione.

8. A diazabicyclo(2,2,2)octadione as defined by claim 1, wherein said diazabicyclo(2,2,2)octadione is 1-ethyl-2,6-diazabicyclo(2,2,2)octa-3,5-dione.

9. A diazabicyclo(2,2,2)octadione as defined by claim 1, wherein said diazabicyclo(2,2,2)octadione is 1,8-dimethyl-2,6-diazabicyclo(2,2,2)octa-3,5-dione.

* * * * *